United States Patent [19]

Argentar

[11] 4,390,714
[45] Jun. 28, 1983

[54] TERTIARY AROMATIC AMINE ACCELERATORS IN ACRYLIC RESIN

[75] Inventor: Harold Argentar, Rockville, Md.

[73] Assignee: American Dental Association Health Foundation, Chicago, Ill.

[21] Appl. No.: 166,383

[22] Filed: Jul. 7, 1980

Related U.S. Application Data

[62] Division of Ser. No. 885,275, Mar. 10, 1978, Pat. No. 4,243,763.

[51] Int. Cl.$^3$ .................................................. C07C 101/72
[52] U.S. Cl. ..................................... 560/36; 549/551; 560/19; 560/45; 560/48; 560/50; 560/221; 562/433; 562/441; 562/452; 562/457
[58] Field of Search ............... 560/45, 221, 19, 36, 560/45, 48, 50; 528/98; 260/348.44; 562/433, 441, 452, 457; 549/551

[56] References Cited

U.S. PATENT DOCUMENTS 4,119,609 10/1978 Allen et al. ............................ 528/98
4,268,656 5/1981 Ray-Chaudhuri et al. ........... 528/98

Primary Examiner—Michael L. Shippen
Attorney, Agent, or Firm—Allegretti, Newitt, Witcoff & McAndrews, Ltd.

[57] ABSTRACT

Tertiary aromatic amines derived from aminoglutethimide or para-aminophenylacetic acid act as accelerators for the peroxide catalyzed polymerization of acrylic resins, especially methacrylates, acrylates and unsaturated polyesters. The amines are characterized by good hardening, strength, color and toxicity characteristics, and are thereby particularly suited for use in the filling and restoration of human teeth and the cementing of bone.

3 Claims, No Drawings

TERTIARY AROMATIC AMINE ACCELERATORS IN ACRYLIC RESIN

This is a division of application Ser. No. 885,275, filed Mar. 10, 1978, now U.S. Pat. No. 4,243,763.

BACKGROUND OF THE INVENTION

1. Field of the Invention

This invention relates to certain tertiary aromatic amines which are unique in their application as accelerators for the peroxide catalyzed polymerization of acrylic resins. The tertiary aromatic amine accelerators of the present invention are derived either from aminoglutethimide or from para-aminophenylacetic acid. The polymerized acrylic resin compositions are particularly useful in dentistry as improved restorative materials, with or without the addition of reinforcing fillers, and in medicine as orthopedic bone cements.

2. Background of the Invention

Aminoglutethimide, the basic compound from which one class of the amines of the present invention are derived, is known in the literature as an anticonvulsant and potent inhibitor of steroid biosynthesis, rather than as an accelerator for peroxide catalyzed acrylic resin polymerization. Hanson, Ballonoff and Northcutt, 230 *J. Am. Med. Assn.* 963 (1974); *The Merck Index* 56 (8th ed. Stecher 1968); U.S. Pat. No. 2,848,455. With respect to the second class of tertiary aromatic amines employed in the present invention, the lower molecular weight homologues of the amines derived from para-aminophenylacetic acid are recognized in the literature as having limited usefulness as chemical intermediates and anti-inflammatory agents, rather than as polymerization accelerators. Everett, Roberts and Ross, *J. Chem. Soc.* 2386 (1953); Tadros, Sakla and Awad, 315 *J. Prakt. Chem.* 1002 (1973); Tuzun, 13 *Commun. Fac. Sci., Univ. Ankra, Ser. B. Chim.* 41 (1966); Wall, Abernathy, Carroll and Taylor, 12 *J. Med. Chem.* 810 (1969); U.S. Pat. Nos. 3,789,123 and 3,657,230; German Patent Nos. 1,913,742 and 2,223,855.

The use of other selected amines, especially simple amines, in conjunction with peroxides to bring about polymerization of acrylic resins has been known since 1940 or earlier. See German Pat. No. 760,351 to E. Schnebel. Certain acrylic resin/peroxide/aromatic amine polymerization systems have been employed in the past in the dental and medical arts. See for example, *Guide to Dental Materials and Devices* 113 (7th ed. 1974–75); *Guide to Dental Materials and Devices* 112 (6th ed. 1972–73); Lal and Green, 17 *J. Polym. Sci.* 403 (1955); F. Peyton and R. Craig, *Restorative Dental Materials* 441 (4th ed. 1971); R. Phillips, *Skinner's Science of Dental Materials* 193–94, 219–20 (7th ed. 1973); U.S. Pat. No. 2,558,139. A peroxide-free system is shown in U.S. Pat. No. 3,541,068. Tertiary amines with an aniline skeleton and higher molecular weight nitrogen substituents are suggested for use in dental materials in U.S. Pat. No. 3,740,850, Bowen and Argentar, 50 *J. Dent. Ref.* 923 (1971), and Bowen and Argentar, 51 *J. Dent. Ref.* 473 (1972). The use of tertiary amines as accelerators in conjunction with ethylenically unsaturated monomers and catalysts in other technological areas, such as in the areas of ink vehicles, wax compositions, metal adhesives, coatings and anaerobic sealants are shown in U.S. Pat. Nos. 3,966,573; 3,790,541, 3,629,220; 3,634,379; 3,594,354 and 3,682,875. See also Mleziva, 15 *Chem. Prum.* 80 (1965); Mleziva, 1 *Plast. Hmoty. Kauc.* 225 (1964); U.S. Pat. Nos. 3,631,009; 3,525,725.

However, as has been documented in the literature, the aromatic amines previously used for acceleration of the peroxide catalyzed polymerization of acrylic resins have been characterized by a number of major disadvantages with respect to their use especially in dental materials. Some fail to cause rapid hardening at room temperature, a necessary property for a resin composition which is to be employed in medical or dental work. A number result in composites with poor resistance to mechanical wear, which is a serious drawback in a dental material which will be subjected to the pressures of chewing and grinding.

In general, the amines used previously have tended to introduce undesirable coloration into the dental material upon initiation of polymerization. See Bowen and Argentar, 51 *J. Dent. Res.* 473 (1972); Bowen and Argentar, 50 *J. Dent. Res.* 923 (1971); Bowen and Argentar, 75 *J. Amer. Dent. Assn.* 918 (1967); Brauer, Davenport and Hansen, 34 Mod. Plast. 153 (1956). Prior art accelerators have also exhibited lack of color stability upon exposure of the specimen containing the compound to either visible or near-visible ultraviolet light (such as sunlight) over a period of time. Such exposure would occur as a matter of course for resin compositions employed as dental materials. Since the cosmetic appearance of restorative dental work (e.g., crowns) is very important to the patient, these difficulties are of considerable concern in the field of dentistry.

Furthermore, it is suspected that, because of their toxicity, aromatic amines are involved in eliciting an unfavorable dental pulp response to the final polymerized resin composition. See Bowen and Argentar, 51 *J. Dent. Res.* 473 (1972); U.S. Pat. No. 3,740,850. The toxicity of the amines to surrounding tissues would also be an important consideration in choice of orthopedic bone cements.

SUMMARY OF INVENTION

The psychological importance to the patient of the appearance of replacement teeth and practical importance of comfort and decreased need for re-replacement make reduced discoloration tendency and tissue irritation coupled with high mechanical strength of key importance in dental resin formulations. An aromatic amine that is very reactive could be employed to bring about polymerization or curing of acrylic resins within an acceptable time period in a concentration much lower than that required for other amines. If the tendency toward amine discoloration and toxicity is not related to the reactivity of the amine with peroxides, then the discoloration tendency and possible tissue irritation of a resin formulation containing an especially reactive amine in the reduced quantity required would accordingly be reduced in comparison to those formulations containing other amines.

It has now been found that the nitrogen substituents play less of a role in governing the behavior of a tertiary aromatic amine than do the aromatic substituents, and that a correlation of the reactivity of aromatic amines (for amines at the same initial molar concentration) possessing the same nitrogen substituents with the electron-donating abilities of the variable aryl substituents as measured by the total $\sigma^+$ value of the substituent(s) indicates that a $\sigma^+$ value for the ring substituent of between $-0.05$ and $-0.40$, preferably approximately $-0.20$, is optimal. This correlation is useful primarily with respect to meta- and para-substituents. The definition of σ+ and examples of its use for correlating certain properties of aromatic amines as given in Argentar, 80A *J. Res. Nat. Bur. Stand.* (U.S.) 178 (1976), is incorporated herein by reference. The invention here described makes use of a polymerization system containing a class of tertiary aromatic amines possessing ring substituents with approximately this characteristic σ+ value.

The first type of tertiary aromatic amines forming a part of the present invention are derived from aminoglutethimide and are selected from the following:

(A) 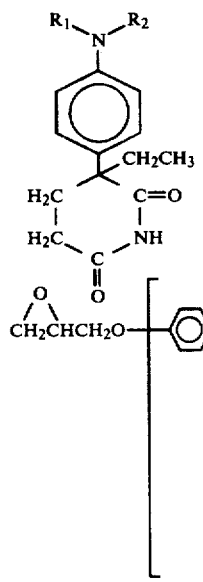

where $R_1$ and $R_2$ are the same or different and are selected from the following groups:

(a) —CH$_3$, (b) —CH$_2$CH$_2$ C$_n$H$_{2n+1}$ with n varying between 0 and 18, (c) 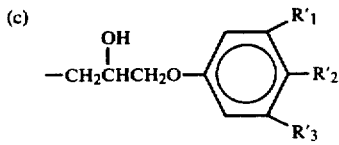

were $R_1'$, $R_2'$ and $R_3'$ are each either hydrogen, normal alkyl, —C$_n$H$_{2n+1}$, with n varying between 1 and 20, or t-butyl, but if one R' is t-butyl, then the adjacent R' is hydrogen, (d) 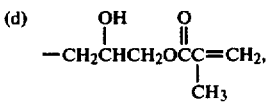

(e) 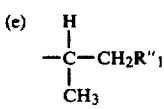

where $R_1''$ is —C$_n$H$_{2n+1}$ with n varying from 0 to 17, or (f) —CH$_2$CH$_2$OH; or (B) a polymeric amine having 10 or fewer amine units which is the reaction product of the amine (A) in which $R_1$ and $R_2$ are each hydrogen with the diglycidyl ether of bisphenol A, viz.,

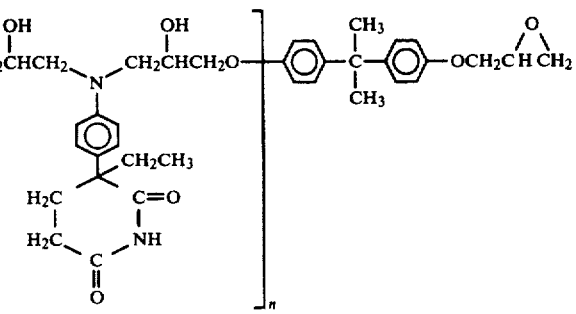

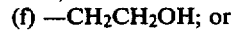

where n varies between 1 and 10, or the hydrolysis product of this polymeric amine, viz.,

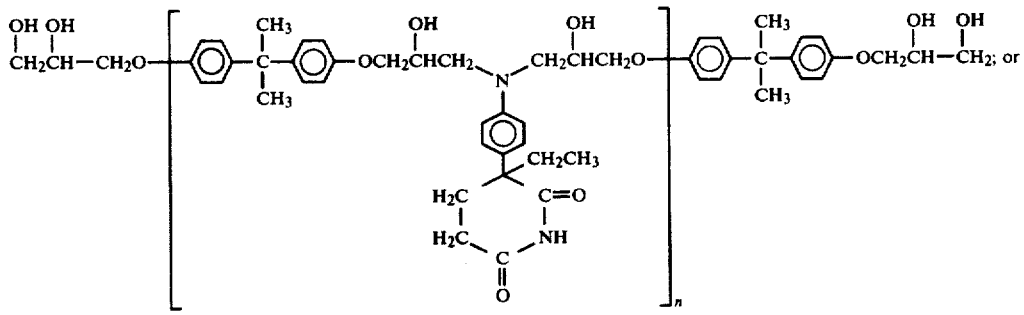

where $R_1$ and $R_2$ are the same or different and are selected from the following groups:

(C) a polymeric amine having a chain of type (B) but having terminal amine groups of type (A), where $R_1$ or $R_2$ for these terminal groups is as defined in (A); or (D) a polymeric amine having 10 or fewer amine units which is the reaction product of the amine (B) with methacrylic or acrylic acid.

The second type of amines employed in the present invention are tertiary aromatic amines derived from para-aminophenylacetic acid and are selected from the following:

(A) 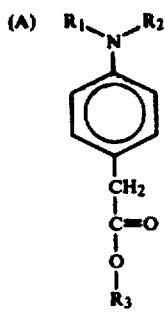

where $R_1$ and $R_2$ are the same or different and are selected from the following groups:

(a) —$CH_3$, (b) —$CH_2CH_2\ C_nH_{2n+1}$ with n varying between 0 and 18, (c) 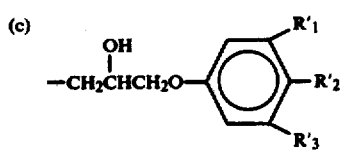

where $R_1'$, $R_2'$ and $R_3'$ are each either hydrogen, normal alkyl, —$C_nH_{2n+1}$, with n varying between 1 and 20, or t-butyl, but if one R' is t-butyl, then the adjacent R' is hydrogen, (d) 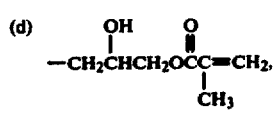

(e) 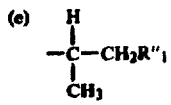

where $R_1''$ is —$C_nH_{2n+1}$ with n varying from 0 to 17, or (f) —$CH_2CH_2OH$; or (B) a polymeric amine having 10 or fewer amine units which is the reaction product of the amine (A) in which $R_1$ and $R_2$ are each hydrogen with the diglycidyl ether of a bisphenol A, viz.,

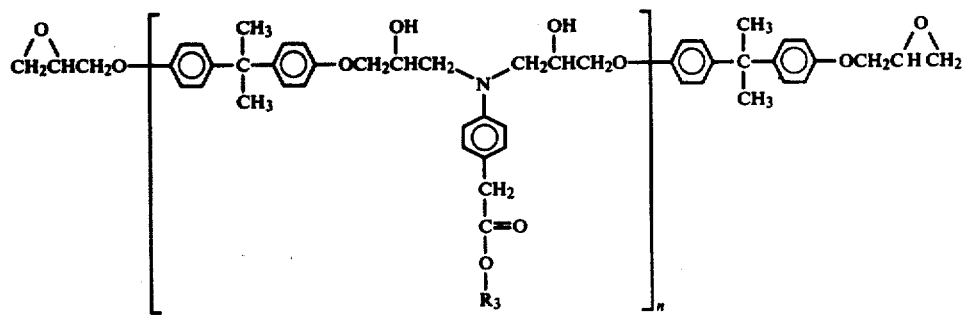

where n varies between 1 and 10, or the hydrolysis product of this polymeric amine, viz.,

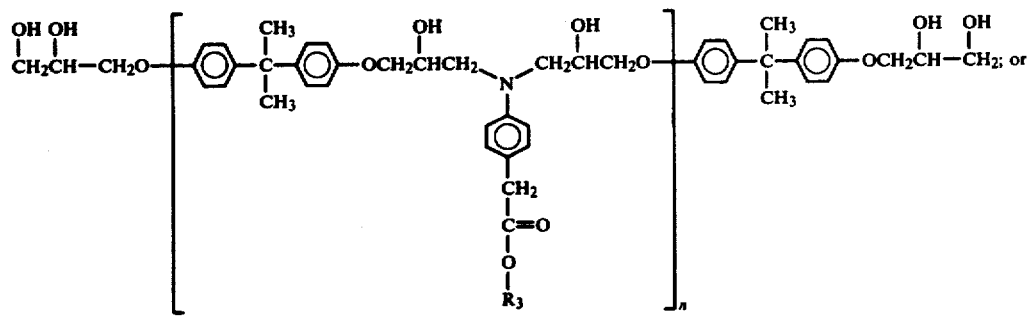

(C) a polymeric amine having a chain of type (B) but having terminal amine groups of type (A), where $R_1$ or $R_2$ for these terminal groups is as defined in (A); or (D) a polymeric amine having 10 or fewer amine units which is the reaction product of the amine (B) with methacrylic or acrylic acid; or (E) an amine having the formuula

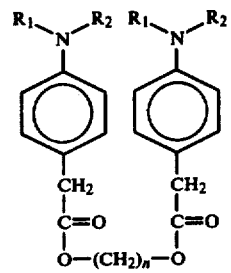

where $R_1$ and $R_2$ are as defined in subpart (A) but with no greater than 5 carbon atoms in the alkyl substituents of $R_1$ and $R_2$, and where n varies between 1 and 20; or (F) a polymeric amine having the formula

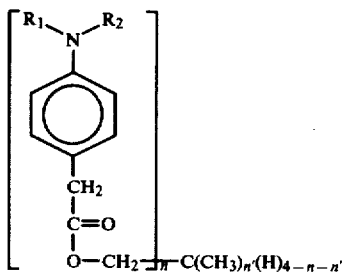

where $R_1$ and $R_2$ are as defined in subpart (A) but with no greater than 5 carbon atoms in the alkyl substituents of $R_1$ and $R_2$, and where n varies between 2 and 4, and n' varies between 0 and 4-n;

and where $R_3$ is in each instance selected from one of the following groups:

(1) —$CH_3$,

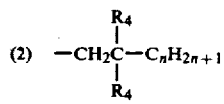

where $R_4$ is hydrogen or methyl and n varies between 0 and 18, (3) —CHCH$_2$C$_n$H$_{2n+1}$
       |
       CH$_3$ (4) the substituents of subparts (A)(c), (A)(d) and (A)(f), (5) and in the case of amines of type (A), —H.

In general, the invention involves these two groups of tertiary aromatic amines, in most instances believed novel in their own right, and their use as polymerization accelerators in the peroxide catalyzed polymerization of acrylate esters, methacrylate esters and unsaturated polyesters. All of the aminoglutethimide derivatives and at least those para-aminophenylacetic acid derivatives in which at least one of $R_1$ and $R_2$ is of structural type (c) or (d) or the compound is of structural type (B), (C), or (D) are believed novel in and of themselves. In a preferred form of the invention, the tertiary aromatic amines are employed in a restorative dental material or bone cement comprising a methacrylate ester, a diacyl peroxide catalyst and the amine. Particularly when employed in a method of treating human teeth for filling and for restorative purposes, the amine-containing composition contacted with the teeth may further comprise a reinforcing filler of the type routinely used in the dental field.

DETAILED DESCRIPTION OF INVENTION

The tertiary aromatic amines employed in the present invention may be used individually or in combination, with total accelerator concentration generally falling within the range of 0.1 to 2.0% by weight of the entire polymerizable mass. While the definitions of these tertiary aromatic amines are believed self-explanatory, formulas for representative compounds will be provided to aid in their visualization. An example of an aminoglutethimide derivative of type (C) is the following:

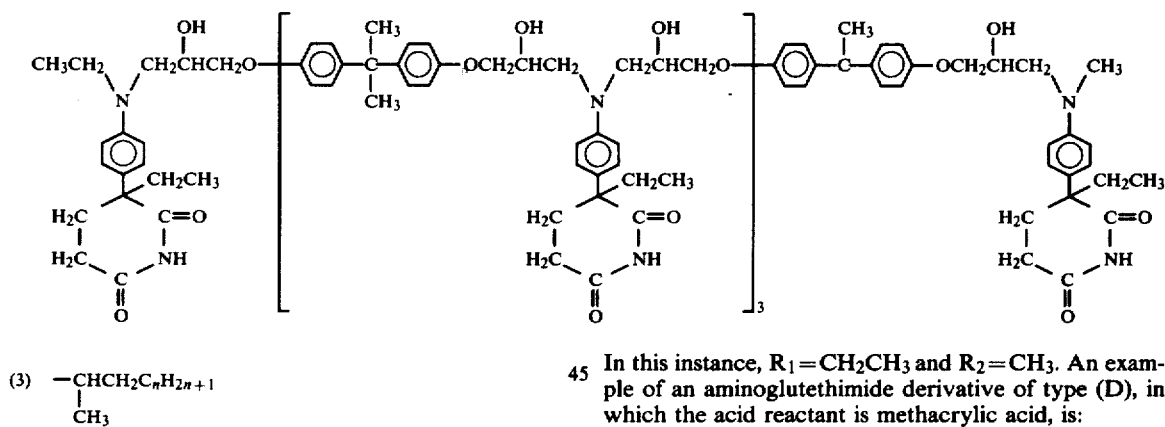

In this instance, $R_1 = CH_2CH_3$ and $R_2 = CH_3$. An example of an aminoglutethimide derivative of type (D), in which the acid reactant is methacrylic acid, is:

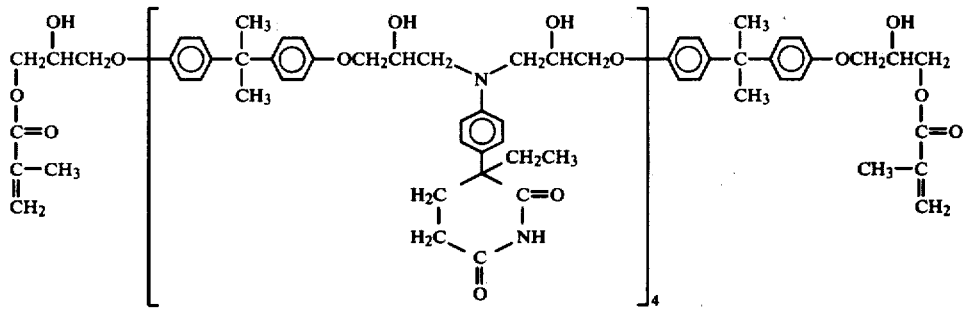

And a representative polymeric amine of type (E) derived from para-aminophenylacetic acid is the following, in which $R_1 = R_2 = CH_2CH_2OH$, and n is 2:

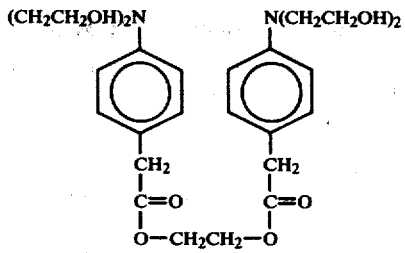

The monomeric pre-polymers polymerized in the practice of the present invention may include separately or in mixtures the various esters of methacrylic acid and acrylic acid, and unsaturated polyesters, such as those derived from maleic acid. The preferred monomers for use in dental applications are the methacrylates, and primarily the dimethacrylates. The acrylate esters may tend to be somewhat more toxic than the methacrylate esters.

Suitable initiators for the free-radical polymerization of these monomers are the peroxides, especially the diacyl peroxides, and in particular lauroyl and benzoyl peroxide. The catalysts may be employed alone or in mixtures with one another. Any suitable amount of the initiator may be used, but in general a satisfactory catalyst concentration falls within the range of 0.1 to 2.0 percent by weight of the entire polymerizable mass.

Reinforcing fillers are employed as a component of the polymerizable mass in certain applications of the invention, especially in the preparation of restorative dental materials. Many such fillers for dental material are known in the art; any appropriate filler which improves the characteristics of the formulation may be utilized. At present, a preferred reinforcing filler is fused silica in conjunction with a silane keying agent.

In some instances, it may also be desirable to include a polymerization inhibitor or a stabilizing agent such as butylated hydroxytoluene (BHT) in the polymerizable mass in order to prevent premature polymerization of the composition prior to its use.

The following Examples illustrate the preparation, use and comparative evaluation of a number of the tertiary aromatic amines of the instant invention.

EXAMPLE 1

Synthesis of Methyl p-dimethylaminophenylacetate
(Methyl 4-N,N-dimethylaminophenylacetate)
(MDMAPA)

Para-aminophenylacetic acid in the amount of 7.55 g (0.05 mol) is heated with 12 g (0.08 mol) of iodomethane and 27 g (0.19 mol) potassium carbonate in dimethyl sulfoxide for 4 hours at 110° C. The product is separated from the reaction mixture by acidification and extraction with $CH_2Cl_2$. After evaporation of the solvent and vacuum distillation, a nearly colorless liquid of boiling point 107° C. at 1 mm, $n_D^{23} = 1.5431$, is obtained in a yield of 4.0 g (26%). IR and NMR spectra confirm its structure as MDMAPA.

EXAMPLE 2

The above synthesis is repeated on a larger scale using no excess iodomethane. The resulting yield is poorer.

EXAMPLE 3

Comparison of MDMAPA With Other Accelerators

The MDMAPA synthesized according to Examples 1 and 2 is compared with N,N-dimethyl-p-toluidine (I), N,N-dihydroxyethyl toluidine (II) and N,N-dimethyl-sym-xylidine (III). The accelerating efficiency of MDMAPA in the benzoyl peroxide-initiated polymerization of methyl methacrylate is somewhat lower than that of I, II or III. The resulting MDMAPA-containing resins show less color than those accelerated with I, but more color than those accelerated with II or III. The biocompatibility of MDMAPA is predicted to be superior.

EXAMPLE 4

Synthesis of Methyl p-dimethylaminophenylacetate
(MDMAPA) and 4-N,N-Dimethylaminophenylacetic
acid (DMAPAA)

Seven and one-half grams (0.05 moles) 4-aminophenylacetic acid, 18.4 g (0.15 moles) iodomethane (methyl iodide) and 27.0 g (0.20 moles) anhydrous potassium carbonate in 75 ml. dimethyl sulfoxide are heated between 100° and 110° C. for 7 hours. The methyl ester is separated from the reaction mixture by acidification with concentrated HCl and then extracted several times with methylene chloride. After the evaporation of this solvent and vacuum distillation of the residue, a faintly yellow, slightly viscous liquid is obtained with a boiling point of 107° C. at $1.3 \times 10^2$ Pa (1 mm. Hg). The yield of the product is 2.5 g (26%). The assigned structure of this compound is confirmed by NMR and IR analyses.

The black residue from the vacuum distillation, containing the bulk of the free acid, is dissolved in methylene chloride and extracted with three 100 ml. portions of 10% potassium carbonate solution. The basic extracts are combined, neutralized, and re-extracted with three 100 ml. portions of methylene chloride. The free acid is obtained after concentration of the combined methylene chloride extracts. The crude product is recrystallized from water, forming a white solid (m.p.=110°-112° C.). The yield is about 55%. The assigned structure is confirmed by NMR and IR analyses.

EXAMPLE 5

Synthesis of Ethylene Diester of
4-N,N-Di-(2-propyl)-aminoglutethimide

4-N,N-di-(2-propyl)-aminoglutethimide is prepared from aminoglutethimide and an isopropyl halide. The resultant compound in the amount of 0.03 mol is refluxed with ethylene glycol in excess (6.2 g, 0.1 mol) in toluene in the presence of a strong acid catalyst. Water is removed. Substantial conversion to the ethylene diester of 4-N,N-(2-propyl)-aminoglutethimide is obtained.

EXAMPLE 6

Synthesis of the Methacrylate Condensation Product of
the n-Butylaminophenylacetate Adduct of the
Diglycidyl Ether of Bisphenol A A polymeric amine having between 1 and 8 amine units is prepared by the addition of the diglycidyl ether of bisphenol A to n-butyl p-aminophenylacetate. Reflux of this product in excess with methacrylic acid in the presence of BHT results in a substantial yield of the desired adduct.

EXAMPLE 7

The synthesis of the diglycidyl ether of bisphenol A/n-butyl p-aminophenylacetate polymeric amine is repeated as in Example 6. The resulting product is then refluxed with an excess of N-(2-hydroxy-3-phenoxypropyl)aminoglutethimide in aqueous ethanol for several hours. The resulting polymeric amine has terminal amine units in the N-(2-hydroxy-3-phenoxypropyl)aminoglutethimide form.

EXAMPLE 8

Synthesis of N,N-Dimethylaminoglutethimide (DMAG)

(a) Synthesis of the N,N,N-trimethylammonium iodide salt of aminoglutethimide (I): Five grams of aminoglutethimide (0.0215 moles) are heated with 18.3 g iodomethane (1.189 moles) and 5.5 g sodium bicarbonate (0.0215 moles) in the presence of a mixed solvent of 1:1 ethanol-water. The reaction mixture is allowed to reflux for 4 hours, forming the quaternary ammonium iodide salt. The product, m.p.=198°-200° C., is recrystallized from acetone.

(b) Synthesis of N,N,N-trimethylammonium acetate salt of aminoglutethimide (II): One gram (2 millimoles) of (I) is heated with 0.3 g (3 millimoles) potassium acetate and 5 ml methanol. After the solids are dissolved in the methanol, 30 ml. toluene are added and the reaction mixture is refluxed for 24 hours, forming the ammonium acetate salt, which is not isolated.

(c) Conversion of (II) to N,N-dimethylaminoglutethimide (III): After continued refluxing of (II) for about 7 hours, the toluene is allowed to evaporate. A beige solid is recovered, m.p.=142°-144° C. The assigned structure of this compound (III) is confirmed by NMR and IR analyses.

EXAMPLE 9

Alternative Synthesis of DMAG

In this improved method, the acetate salt of N,N,N-trimethylaminoglutethimide is formed directly from the starting material.

(a) Synthesis of the N,N,N-trimethylammonium acetate salt of aminoglutethimide (II): Five grams aminoglutethimide (0.0215 moles) and 10 g potassium acetate (0.1075 moles) are heated in the presence of methanol and 18.3 g iodomethane (0.189 moles). The reaction mixture is refluxed for 7 hours. The methanol is driven off and the acetate recrystallized from methylene chloride. The white solid, m.p.=168°-170° C., is characterized by infrared analysis.

(b) Conversion of (II) to N,N-dimethylaminoglutethimide (III): (II) is refluxed for 7 hours with toluene as the diluent as described in Example 8. The beige solid is recrystallized (CH₃OH) after treatments with decolorizing charcoal. The white solid, m.p.=142°-144° C., is characterized as before.

EXAMPLE 10

Comparison of DMAPAA, MDMAPA and DMAG With Other Polymerization Accelerators In this Example, the characteristics of MDMAPA and DMAG are compared with the characteristics of a number of amines used commercially in composites (N,N-dimethyl-p-toluidine, N,N-dihydroxyethyl-p-toluidine and N,N-dimethylsym-xylidine) and with several other amines synthesized for the purpose of comparison. The amines evaluated, their abbreviated names and their sources are summarized in Table 1.

TABLE 1

| Tertiary Aromatic Amine Accelerators Evaluated | | | |
|---|---|---|---|
| Amine Accelerator | Abbreviation | Grade | Source |
| Methyl 4-N,N—Dimethylaminophenylacetate | MDMAPA | b.p. = 107° C. at 1 mm. | Synthesized |
| N,N—Dimethylaminoglutethimide | DMAG | m.p. = 142-144° C. | Synthesized |
| N,N—Dimethyl-p-toluidine | DMPT | | Commercial |
| N,N—Di-2-Hydroxyethyl-p-toluidine | DHEPT | | Commercial |
| N,N—Di-2-hydroxypropyl-p-toluidine | DHPPT | m.p. = 109-110° C. | Commercial |
| N,N—Dimethyl-sym-xylidine | DMSX | b.p. = 100-103° C. at | Commercial |
| N,N—Bis(3-p-tolyloxy-2-hydroxypropyl)-m-xylidine (low melting and high melting isomers) | BTX | low melting: m.p. = 102.5-106° C. high melting: m.p. = 145.5-148° C. | Synthesized |
| 4-N,N—Dimethylaminobenzaldehyde | 4-DMAB | m.p. = 73-75° C. | Commercial |
| 4-N,N—Dimethylaminobenzoic acid | 4-DMABA | m.p. = 241° C. | Commercial |
| Tetramethylammonium 4-N,N—dimethylaminobenzoate | TMADMAB | melts with decomposition | Synthesized |
| Lithium 4-N,N—dimethylaminobenzoate | LDMAB | melts with decomposition 210° C. | Synthesized |
| 3-N,N—Dimethylaminobenzoic acid | 3-DMABA | m.p. = 150-152° C. | Commercial |
| 4-N,N—Dimethylaminophenylacetic acid | DMAPAA | m.p. = 110-112° C. | Synthesized |
| Poly SAM-1 | PSAA | m.p. = 81-92° C. | Synthesized |
| 4-N,N—Dimethylaminopyridine | DMAP | m.p. = 112-113° C. | Commercial |

The synthesis of BTX is described in Bowen and Argentar, "Tertiary Aromatic Amine Accelerators with Molecular Weights Over 400," 41 *J. Dent. Res.* 473-82 (1972), and that of PSAA is taught in Antonucci and Bowen, "Adhesive Bonding of Various Materials to Hard Tissues XIII, The Synthesis of a polyfunctional Surface-Active Amine Accelerator," *J. Dent. Res.* (in press). The syntheses of TMADMAB and LDMAB are set forth in Examples 11 and 12.

An experimental powder-liquid polymerizable formulation is used to test the various amine accelerators. The liquid component contains 70% bis-(3-methacryloxy-2-hydroxypropyl) bisphenol-A (Bis-GMA), 30% triethylene glycol dimethacrylate or 2-hydroxyethyl methacrylate and triethyleneglycol dimethacrylate as the diluent monomer, 0.2% butylated hydroxytoluene as an inhibitor, and varying concentrations of tertiary amine accelerators. When possible, nearly equal molal concentrations of the different amines are incorporated into the liquid.

The powder component of the polymerizable formulation is prepared by placing spherical silica (200 g) and barium flouride-containing glass (100 g) both treated with gamma-methacryloxypropyltrimethoxysilane in a round-bottomed flask and covering these components with 300 ml methylene chloride containing one percent benzoyl peroxide. The diluent is removed by rotary evaporation under gradually increasing vacuum. The flask is kept on the rotary evaporator for 48 hours to insure complete evaporation of the diluent and proper coating of the silanized glass beads with benzoyl peroxide. Composites are formulated with the amine accelerators using a 3:1 powder-liquid ratio.

Tests for working time, diametral tensile strength, color stability and water sorption are conducted according to American Dental Association Specification No. 27. See "Council on Dental Materials and Devices, New American Dental Association Specification No. 27 for Direct Filling Resins," 94 *JADA* 1191-94 (1977). Hardening time is measured as outlined in American Dental Association Specification No. 8. See "American Dental Association: American Dental Association Specification No. 8 for Dental Zinc Phosphate Cement," *Guide to Dental Materials and Devices* 189-93 (7th ed. 1974). Compressive strength is determined using the same powder-liquid ratio (0.45 g:0.15 g) and the same dimensions as employed in the diametral tensile strength tests. Measurements are obtained with a universal testing machine at a crosshead speed of 1.25 cm/min. In the color stability test, a Westinghouse RS light source is used. Visual evaluation of the color changes is made in a "blind test" by three observers. The water sorption specimens are prepared using 0.9 g powder and 0.3 g liquid.

The results of the comparative tests are summarized in Table 2.

TABLE 2

Properties of Tertiary Aromatic Amine Accelerators

| Amine | Mol. Wt. | Amine Concentration Weight % | mMolal | Hardening Time Min. | Setting Time Min. | Tensile Strength MPa[b] | Compressive Strength MPa[b] | Color Stab. |
|---|---|---|---|---|---|---|---|---|
| MDMAPA | 193 | 0.16 | 8.3 | — | 6.0 | 38.6(2.8) | 147.4(16.0) | 3 |
| — | | 0.24 | 12.4 | — | — | 47.1(4.2) | — | — |
| — | | 0.32 | 16.6 | 2.5 | 3.0 | 49.6(2.2) | 190.7(9.4) | — |
| DMAG | 260 | 0.48 | 18.5 | 2.5 | 3.5 | 37.7(0.5) | 198.0(7.6) | 4 |
| — | | 0.61 | 23.5 | 3.0 | 3.5 | 43.6(2.4) | 221.2(12.6) | 3.5 |
| — | | 0.87 | 33.5 | — | 2.0 | 27.1(2.6) | 177.7(9.6) | — |
| — | | 1.22 | 46.9 | — | 2.0 | 30.6(1.0) | 191.3(15.4) | — |
| DMPT | 135 | 0.14 | 10.2 | — | 6.0 | 23.4(4.8) | 147.7(12.2) | 3.5 |
| — | | 0.23 | 17.0 | 3.5 | 4.5 | 44.8(1.7) | 194.4(3.6) | 2 |
| — | | 0.23 | 17.0 | — | 4.0 | — | — | — |
| — | | 0.28 | 20.7 | — | 5.0 | 28.2(6.2) | 152.9(25.0) | — |
| — | | 0.32 | 23.7 | — | 1.5 | — | — | — |
| — | | 0.45 | 33.3 | — | 1.0 | — | — | — |
| DHEPT | 195 | .26 | 13.3 | — | 12.5 | — | — | — |
| — | | .32 | 16.4 | 13 | 8. | 43.7(1.6) | 191.5(5.3) | 3 |
| — | | .66 | 33.8 | — | 6. | 33.8(7.0) | 171.3(9.1) | — |
| DHPPT | 211 | .35 | 16.6 | — | 8.5 | 39.5(2.2) | 198.9(14.1) | 3 |
| DMSX | 149 | .15 | 10.1 | — | 2.5 | 27.3(5.2) | 174.4(13.2) | 3.5 |
| — | | .20 | 13.4 | — | 3.0 | 32.4(1.8) | — | — |
| — | | .25 | 16.8 | 2.0 | 2.5 | 48.7(3.3) | 186.7(6.2) | 3 |
| — | | .30 | 20.1 | — | 3.0 | 30.3(5.1) | 163.6(12.9) | — |
| — | | .40 | 26.8 | — | 1.0 | — | — | — |
| — | | .50 | 33.6 | — | 3.0 | — | 156.7(20.8) | — |
| BTX Low Melting | 450 | .76 | 16.9 | — | 8.5 | 36.9(2.3) | 201.2(12.4) | 3 |
| BTX High Melting | 450 | .76 | 16.9 | — | 9.0 | 38.1(3.5) | 198.5(5.9) | 4 |
| DMAB | 149 | .25 | 16.8 | — | 20+ | — | — | — |
| 4-DMBA | 165 | .28 | 17.0 | — | 6.5 | 40.9(6.4) | 197.5(14.1) | 2 |
| — | | .55 | 33.3 | — | 9.0+ | — | — | — |
| —[c] | | .28 | 17.0 | — | 8 | 36.1(6.0) | 192.6(13.9) | 2 |
| TMADMAB | 238 | .39 | 16.4 | — | 4.0 | 41.7(1.3) | 192.3(15.4) | 2 |
| — | | .96 | 40.3 | — | 4.5 | 29.5(1.0) | 177.3(10.4) | 2.5 |
| — | | 1.28 | 53.8 | — | 5.0 | 30.9(.6) | 164.6(9.7) | — |
| —[c] | | .39 | 16.4 | — | 4.0 | 40.3(1.8) | 190.4(10.7) | 2 |
| LDMAB[d] | 171 | .29 | 17.0 | — | 4.0 | 41.2(2.0) | 196.2(7.9) | 3 |
| 3-DMABA | 165 | .28 | 17.0 | 15+ | 11.0 | — | — | — |
| — | | .33 | 20.0 | — | 12.0 | — | — | — |
| — | | .78 | 47.3 | — | 11.0+ | — | — | — |
| DMAPAA | 179 | 0.15 | 8.4 | — | 3.5 | 40.8(3.8) | 165.9(9.4) | — |
| — | | 0.225 | 112.6 | — | — | 47.2(1.6) | — | — |
| — | | 0.30 | 16.8 | 2.0 | 2.0 | 50.4(2.7) | 176.3(16.3) | 4 |
| — | | 0.40 | 22.3 | 2— | 1.0 | — | — | — |
| —[e] | | 0.40 | 22.3 | — | 1.5 | 27.7(5.3) | 181.8(13.5) | — |
| PSAA | 2032 | 1.70 | 8.4 | — | 5.5 | 29.8(5.5) | 179.8(13.4) | 2 |

TABLE 2-continued

| | | Properties of Tertiary Aromatic Amine Accelerators | | | | | | |
|---|---|---|---|---|---|---|---|---|
| | | Amine Concentration | | Hardening Time | Setting Time | Tensile Strength | Compressive Strength | Color |
| Amine | Mol. Wt. | Weight % | mMolal | Min. | Min. | MPa[b] | MPa[b] | Stab. |
| — | | 3.41 | 16.8 | 8+ | 8+ | — | — | |
| DMAP | 122 | .21 | 17.2 | — | 16+ | — | — | — |
| DHEMPT + DMAPAA | 50% 50% | .16 .15 | 8.2 8.4 | — | 2.5 | 45.7(6.8) | 215.1(14.7) | — |
| DHEPT + DMAPAA | 80% 20% | .256 .06 | 13.1 3.4 | 1− | 3.5 | 33.2(1.8) | — | — |
| DHEPT + DMAPAA | 95% 5% | .312 .015 | 16.0 0.84 | — | 8 | — | — | — |

[a]Rating scale by visual observation: 1 - very large change to 4 - no change
[b]Numbers in Parentheses indicate estimated standard deviation
[c]Liquid: 70% Bis-GMA, 20% HEMA, 10% TEGDMA, + 0.2% BHT
[d]Liquid: 71.4% Bis-GMA, 14.3% HEMA, 14.3% TEGDMA, + 0.2% BHT
[e]Liquid contains 0.4% BHT Inspection of the Table indicates that none of the accelerators employed ranks highest in all properties. Those polymerized resins formulated with DMAPAA, MDMAPA or DMAG have physical properties generally as good as or better than comparable resins prepared with commercially used amines.

Hardening and Working Times

A minimum working time of 1.5 minutes and maximum hardening time of 8 minutes are desirable in a direct filling resin. Most of the compositions satisfy these criteria. The tabulated data show that the shortest hardening times are obtained with DMAPAA, DMSX and DMPT. The approximate order of the accelerating ability of the respective amines is DMAPAA>DMSX>MDMAPA, DMPT>DMAG>DHEPT.

Tensile Strength

A minimum of 34 MPa is advisable for the tensile strength of composite resins. Practically all the composites pass this specification test.

Generally, composites possess maximum tensile strength when the liquid component of the mixture contains 16.5 to 17.0 mm amine accelerator. When DMAG is used, a somewhat higher amine concentration (approximately 23.5 mm) gives composites with optimum strength. The tensile peaks are sharpest for DMSX and DMPT and appear to be much broader for DMAG. Maximum tensile strength of about 50 MPa is obtained with DMAPAA, MDMAPA and DMSX. The tensile strength values obtained from incorporating DMPT, DHEPT and DMAG ranging from 43.6 to 44.8 MPa are slightly lower.

Compressive Strength

The compressive strengths of the various composite formulations are given in Table 2. With increasing amine concentration in the monomer the compressive strength of the cured resin increases and reaches a maximum in the 17 to 23 mm concentration range. Within the limits investigated, altering the amine concentration results in a much larger percentage change in the tensile strength than in the compressive strength. Thus, raising the amine concentration from 10 to 35 mm increases the tensile strength from 23.4 to 50.4 MPa; i.e. a 115% change, and changes the compressive strength from 147 to 221 MPa; i.e. by only 50%.

Color Stability

The initial shade of the cured specimens varies from greyish to greyish-brown depending on the different amines used. A rating scale based on comparison of exposed to unexposed specimens ranging from 1 (very large change) to 4 (no change) is employed. Inspection of Table 2 indicates that any increase in concentration of amine lowers the color stability of the cured resin. Resins containing DMAG, BTX (high melting) and DMAPAA in concentrations of less than 20 mm have excellent color stability.

EXAMPLE 11

Synthesis of Tetramethylammonium-4-N,N-dimethylaminobenzoate (TMADMAB)

The tetramethyl ammonium salt of 4-N,N-dimethylaminobenzoic acid is prepared as shown:

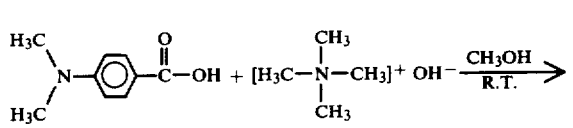

4-N,N—Dimethylaminobenzoic acid

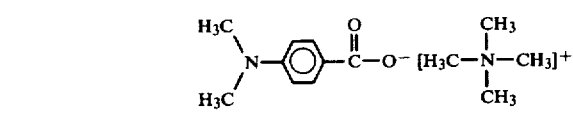

Tetramethylammonium 4-N,N—dimethylaminobenzoate

Tetramethylammonium hydroxide as a 20% solution in methanol (0.1 mole, 9.1 g), 17.0 g 4-N,N-dimethylaminobenzoic acid (0.1 mole) and 100 ml. additional methanol are placed in a round-bottomed flask. After the solution is stirred for 1 hour the methanol is removed by rotary evaporation. The solid mass is then triturated several times with acetone and methylene chloride to give a white solid which has no definite melting point owing to the ready formation of hydrates. The product is characterized by infrared analysis.

EXAMPLE 12

Synthesis of Lithium 4-N,N-Dimethylaminobenzoate (LDMAB)

The lithium salt of 4-N,N-dimethylaminobenzoic acid is prepared as shown:

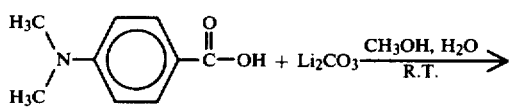

4-N,N—Dimethylaminobenzoic acid

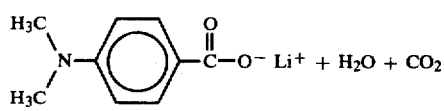

Lithium 4-N,N—dimethylaminobenzoate

4-N,N-dimethylaminobenzoic acid (0.025 moles, 4.13 g) is dissolved in 25-30 ml. methanol. Lithium carbonate (0.0215 moles, 0.925 g) is dissolved in 20-30 ml. water. The two solutions are then combined in a beaker and a white solid precipitated. The mixture is heated for about 4 hours and then transferred to a round-bottomed flask for rotary evaporation. The white solid product is purified using acetone as a triturant. The yield is 52%. The salt shows signs of decomposition above 210° C. The product is characterized by infrared analysis.

EXAMPLE 13

Preparation of Orthopedic Cement

Neopentylglycol dimethacrylate is combined with 0.18 weight % BHT inhibitor and 0.5 weight % pentaerythritol tetrakis(para-dimethylaminophenylacetate). One weight % lauroyl peroxide is added to this mixture to provide a workable bone cement of satisfactory hardening time.

EXAMPLE 14

Preparation of Polymerizable Formulation

2-Hydroxyethyl acrylate and triethyleneglycol dimethacrylate are combined in equal parts. A polymerizable formulation is prepared by the addition thereto of 1.2 weight percent 4-N,N-diethylaminoglutethimide, 0.61 weight % benzoyl peroxide and 0.30 weight % lauroyl peroxide.

EXAMPLE 15

Preparation of Filled Restorative Dental Material

Bisphenol A-glucidyl methacrylate adduct (Bis-GMA) in the proportion of 68% to 32% is combined with triethyleneglycol dimethacrylate; 0.17 weight % BHT, 0.5 weight % p-dimethylaminophenylacetic acid and 0.5 weight % N,N-dimethylamino-p-glutethimide are added. Combined with this in a 1:3 weight ratio is glass originally treated with gamma-methacryloxypropyltrimethoxysilane and 0.9% (as a weight % of the entire polymerizable mass) benzoyl peroxide.

The other tertiary aromatic amines of the present invention may generally be prepared by routes analogous to those detailed in the above Examples, in many instances, by the use of alkyl halides. Attempts to synthesize the ethyl ester of para-aminophenylacetic acid by esterification of the acid in the presence of concentrated hydrochloric acid were unsuccessful. The synthesis of ethyl para-dimethylaminophenylacetate is shown in Romanelli and Becker, "Ethyl para-dimethylaminophenylacetate," 5 Org. Synth. 552-54 (1973).

The preferred tertiary aromatic amines for use in the present invention include those in which $R_1$ and $R_2$ are normal alkyl substituents with between 1 and 5 carbon atoms, and the reaction products of those in which either $R_1$ or $R_2$ or both are hydrogen with glycidyl phenyl ether or glycidyl methacrylate or the diglycidyl ether of bisphenol A. Because of ease of preparation, those amines with $R_1$ and $R_2$ identical are also preferred.

The amines of the present invention may be formed into a composition of matter comprising the polymerizable monomer, a peroxide catalyst and a tertiary aromatic amine. In many instances, it will be desirable to further include a reinforcing filler and/or an inhibitor in this composition. Alternatively, a two component system may be prepared composed of a liquid component and a powder component, wherein the liquid component comprises the polymerizable monomer, tertiary aromatic amine and optional inhibitor, and the powder component comprises the peroxide catalyst and reinforcing filler. The liquid and powder components are combined in order to utilize the composition. The relative quantities of these materials which may be employed vary and may be readily adjusted by one skilled in the art. Representative percentages are indicated in the Examples. For unfilled resins the rate of curing proceeds most rapidly using a molar peroxide to amine ratio between 1.10 and 1.50. For composites a much larger molar excess of peroxide is required to obtain optimum hardening time. This much larger excess of peroxide should be expected since only a small portion of the peroxide is accessible to the amine before the composite is cured.

Preferably, the above-described compositions may be employed as restorative dental materials or as orthopedic bone cement. Thus the tertiary aromatic amines of the present invention are employed in a method of treating human teeth for filling and for restorative purposes which comprises contacting the teeth with a restorative dental material comprising a polymerizable monomer, a peroxide catalyst, and a tertiary aromatic amine of specified formula. Similarly, the invention contemplates a method of cementing bone for restorative purposes by analogous means. In dental and orthopedic applications, polymerization is of necessity a bulk, in situ polymerization with curing at or near room temperature in a period on the order of minutes, preferably within 8 minutes. The compositions containing the tertiary aromatic amines of the present invention satisfy these criteria.

It should be understood that the foregoing disclosure emphasizes certain specific embodiments of the invention and that all modifications or alternatives equivalent thereto are within the spirit or scope of the invention as set forth in the appended claims.

I claim:

1. Tertiary aromatic amines having the following structure:

(A) 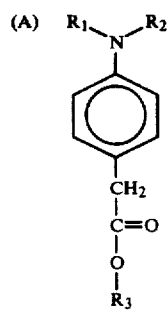

where $R_1$ and $R_2$ are the same or different and are selected from the following groups, with at least one of $R_1$ and $R_2$ always selected from group (c) and (d) or only one of $R_1$ and $R_2$ selected from group (f):

(a) —$CH_3$, (b) —$CH_2CH_2C_nH_{2n+1}$ with n varying between 0 and 18, (c) 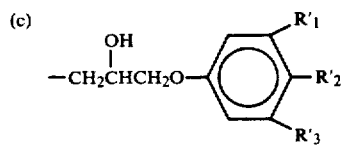

where $R_1'$, $R_2'$ and $R_3'$ are each either hydrogen, normal alkyl, —$C_nH_{2n+1}$ with n varying between 1 and 20, or t-butyl, but if one R' is t-butyl, then the adjacent R' is hydrogen, (d) 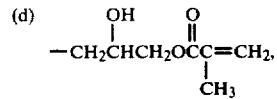

(e) 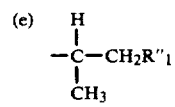

where $R_1''$ is —$C_nH_{2n+1}$ with n varying from 0 to 17, or (f) —$CH_2CH_2OH$; or (B) (1)

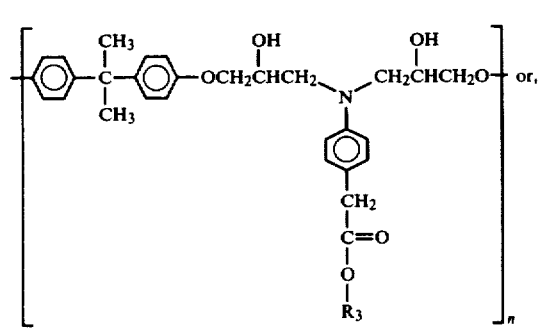

-continued

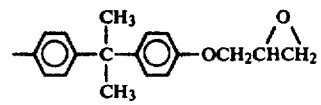

(B) (2)

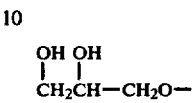

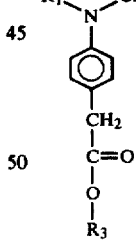

where n in each instance varies between 1 and 10; or (C)

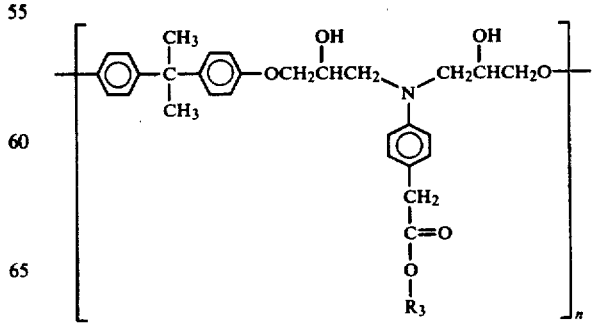

-continued

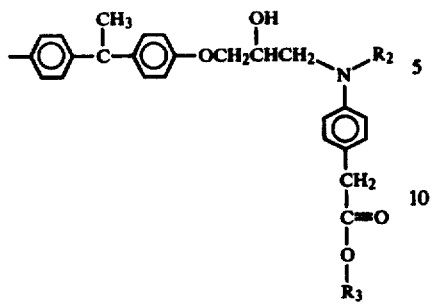

where n varies between 1 and 8, and where $R_1$ and $R_2$ are the same or different and are selected from the following groups:

(a) —$CH_3$, (b) —$CH_2CH_2C_nH_{2n+1}$ with n varying between 0 and 18, (c) 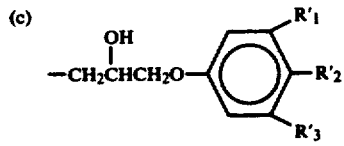

where $R_1'$, $R_2'$ and $R_3'$ are each either hydrogen, normal alkyl, —$C_nH_{2n+1}$, with n varying between 1 and 20, or t-butyl, but if one R' is t-butyl, then the adjacent R' is hydrogen, (d) 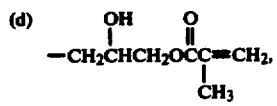

(e) 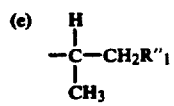

where $R_1''$ is —$C_nH_{2n+1}$ with n varying from 0 to 17, or (f) —$CH_2CH_2OH$; or (D)

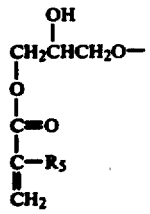

-continued

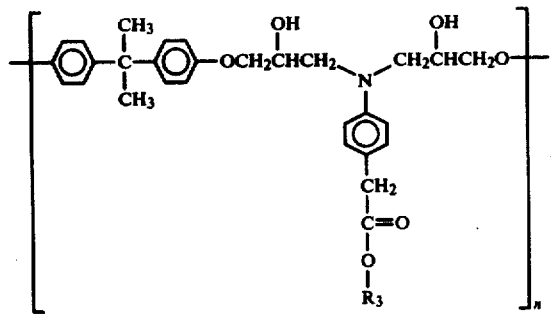

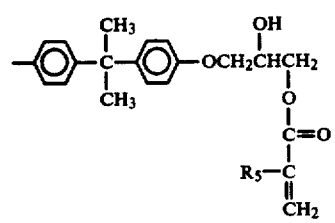

where n varies between 1 and 10 and $R_5$ is hydrogen or —$CH_3$;

and where $R_3$ is in each instance selected from one of the following groups:

(1) —$CH_3$, (2) 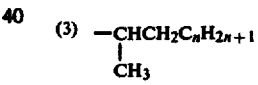

where $R_4$ is hydrogen or methyl and n varies between 0 and 18, (3) 

where n varies between 0 and 17, or (4) the substituents of subparts (A) (c), (A) (d) and (A) (f), (5) and in the case of amines of type (A), —H.

2. Tertiary aromatic polymer amines having the following structure:

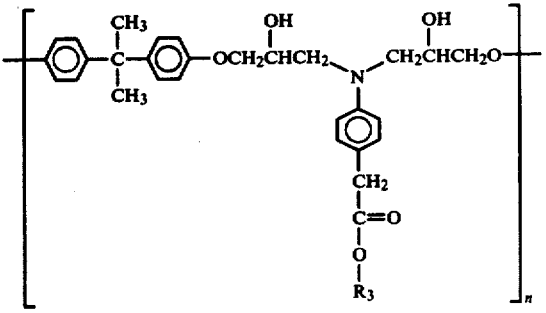

-continued

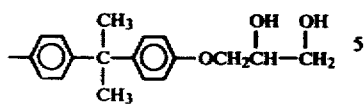

where n in each instance varies between 1 and 10; and where $R_3$ is in each instance selected from one of the following groups:

(1) —$CH_3$,

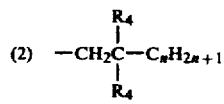

where $R_4$ is hydrogen or methyl and n varies between 0 and 18, (3) —CHCH$_2$C$_n$H$_{2n+1}$
    |
    CH$_3$ where n varies between 0 and 17,

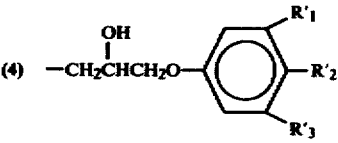

where $R_1'$, $R_2'$ and $R_3'$ are each either hydrogen, normal alkyl, —$C_nH_{2n+1}$ with n varying between 1 and 20, or t-butyl, but if one R' is t-butyl, then the adjacent R' is hydrogen,

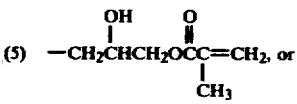

(6) —$CH_2CH_2OH$.

3. A polymeric amine as in claim 2 wherein the amine has two amine units and $R_3$ is —$CH_2CH_3$.

* * * * *